United States Patent [19]
Klapper

[11] Patent Number: 5,846,074
[45] Date of Patent: Dec. 8, 1998

[54] ORTHODONTIC DEVICE FOR CORRECTING OVERBITE AND UNDERBITE

[76] Inventor: Lewis Klapper, 744 Falls Cir., Lake Forest, Ill. 60045

[21] Appl. No.: 40,807

[22] Filed: Mar. 18, 1998

Related U.S. Application Data

[63] Continuation-in-part of Ser. No. 876,667, Jun. 16, 1997, Pat. No. 5,788,486, which is a continuation of Ser. No. 644,848, May 9, 1996, Pat. No. 5,697,782.

[51] Int. Cl.$^6$ ........................................................ A61C 7/36
[52] U.S. Cl. ................................................ 433/19; 433/21
[58] Field of Search .................................... 433/5, 17, 18, 433/19

[56] References Cited

U.S. PATENT DOCUMENTS

| | | | |
|---|---|---|---|
| 3,508,332 | 4/1970 | Armstrong | 433/21 |
| 3,618,214 | 11/1971 | Armstrong . | |
| 3,654,702 | 4/1972 | Kelly, Jr. . | |
| 3,798,773 | 3/1974 | Northcutt . | |
| 4,074,433 | 2/1978 | Nelson | 433/19 |
| 4,416,626 | 11/1983 | Bellavia | 433/7 |
| 4,551,095 | 11/1985 | Mason . | |
| 4,708,646 | 11/1987 | Jasper . | |
| 4,815,968 | 3/1989 | Keller . | |
| 5,167,499 | 12/1992 | Arndt et al. | 433/18 |
| 5,312,247 | 5/1994 | Sachdeva et al. . | |
| 5,352,116 | 10/1994 | West . | |
| 5,435,721 | 7/1995 | Vogt . | |
| 5,443,384 | 8/1995 | Franseen et al. . | |

FOREIGN PATENT DOCUMENTS

| | | | |
|---|---|---|---|
| 2222950 | 3/1990 | United Kingdom | 433/19 |

OTHER PUBLICATIONS

"Mandibular Protraction Appliances for Class II Treatment", Carlos martins Coelho Fiho, DDS, MSD—JCO (May, 1995), vol. XXIX, No. 5, pp. 319–335.

*Primary Examiner*—Cary E. O'Connor
*Attorney, Agent, or Firm*—Welsh & Katz, Ltd.

[57] ABSTRACT

An orthodontic device is worn in the mouth of a patient and is attached between an upper attachment means secured to the maxillary teeth and a lower attachment means secured to the mandibular teeth such that the device is proximal a cheek of the patient. The device is formed from a flexible resilient spring element having a generally curved body portion configured to be inserted in the patient's mouth so as to lie in a plane defined by the cheek of the patient. The spring element has first and second oppositely disposed end portions where the first end portion is configured to be directly attached to corresponding upper or lower attachment means so as to preclude relative movement between the first end portion and the attachment means. The second end portion is configured to be directly attached to the other of the corresponding attachment means. The spring element is operative to produce a pushing force between the upper and lower attachment means when attached thereto where the body portion is configured to be shaped so as to vary the effective length of the spring element to vary the pushing force directed to the maxillary and mandibular teeth so as to displace the maxillary teeth relative to the mandibular teeth. The second end portion terminates in a loop portion configured to attach to the other of the corresponding attachment means.

20 Claims, 4 Drawing Sheets

ORTHODONTIC DEVICE FOR CORRECTING OVERBITE AND UNDERBITE

This is a continuation-in-part of Ser. No. 08/876,667 filed Jun. 16, 1997, entitled Orthodontic Device For Correcting Overbite and Underbite, now U.S. Pat. No. 5,788,486, which is a continuation of Ser. No. 08/644,848 filed May 9, 1996, entitled Orthodontic Device and Method For Correcting Overbite and Underbite, now U.S. Pat. No. 5,697,782 issued Dec. 16, 1997.

BACKGROUND OF THE INVENTION

The present invention relates generally to orthodontic devices for treating various malocclusions including protrusion and retrusion of the upper teeth relative to the lower teeth.

A variety of malocclusions have been corrected with conventionally available orthodontic appliances so that an appropriate alignment is established for the upper teeth, for the lower teeth, and between the upper and lower teeth. Early efforts involved the application of orthodontic appliances to the teeth in conjunction with elastic (rubber) bands to apply appropriate forces to the orthodontic appliances between the upper and lower jaws. Removable headgear for interacting with the teeth is also known to achieve desired movements. Although these techniques have provided satisfactory results, they were found to be subject to certain disadvantages.

One disadvantage of such orthodontic systems is that satisfactory results can only be obtained if a particular device is properly worn. Elastic bands and headgear are easily removed by the patient, thus limiting their overall effectiveness. Headgear has the further disadvantage that since it contacts the neck, it is cosmetically undesirable and therefore less likely to be extensively worn.

Another disadvantage of such orthodontic systems is that they can produce undesirable side effects resulting from undesirable forces that may be applied to the orthodontic appliance in addition to those forces which are desired for an effective treatment to take place. These undesirable forces are most prevalent with elastic bands, at times resulting in tooth extrusion and bite opening. Headgear can also result in tooth extrusion. Elastic bands further have the disadvantage of delivering forces that can decay over time, as the elastic elements stretch and fatigue.

Various devices have been developed in an effort to improve upon the elastic bands and headgear of conventional orthodontic appliances. One such attempt involves the use of spring operated devices, primarily used to replace the elastic bands. Such devices are disclosed for example, in U.S. Pat. Nos. 3,618,214 (Armstrong), and 5,352,116 (West). Generally, such devices employ springs to establish tensions similar to those established by elastic bands. However, in practice, the devices tend to produce relatively severe and undesirable side effects leading to unwanted tooth extrusion and bite opening. Moreover, most available spring-operated devices are removable (much like the elastic bands they replace), and are often not worn, lost, or broken. For those spring-operated devices that are not removable, it is often extremely difficult to clean around such devices. In either case, such devices tend to be bulky, making it difficult for patients to speak and eat with the appliances in place.

Another orthodontic device that has found acceptance is the so-called "bite jumping" appliance. Such appliances are disclosed, for example, in U.S. Pat. Nos. 3,798,773 (Northcutt), 4,551,095 (Mason), and 4,708,646 (Jasper).

One disadvantage of U.S. Pat. No. 4,708,646 issued to Jasper is that it is a multi-part device, requiring a spring element and swivel connections at each end of the spring element. The spring element includes end caps having an aperture through which a metal wire stub is received. The wire stub is fixed to the arch wire at one end, and to a small metal ball at the other end. The end cap swivels about the wire stub and bears against the small round ball. The round metal balls permit the rotation and swiveling motion of the spring element relative to its attachment point. Such multi-part appliances are unduly complex, which increases cost, reduces reliability, and renders cleaning more difficult.

All except U.S. Pat. No. 4,708,646 disclose variations of a device generally known as the "Herbst" device, and include a metal cylinder containing a plunger that is attachable to and between the orthodontic appliances (braces) fixed to the patient's upper and lower teeth. Such devices are rigidly attached to the associated orthodontic appliances and as a result, cannot be removed by the patient. However, because of their rigid attachment, it is not uncommon for such devices to become damaged, or to cause damage to the orthodontic appliances to which they are attached. Primarily, this results from the lack of flexibility of the devices and the relatively large forces that are produced as the patient's jaws are closed in the normal course.

U.S. Pat. No. 4,708,646 replaces the conventional Herbst device with an elastic element comprised of a spring surrounded by a rubber core and having metal end caps for attachment to and between the orthodontic appliances associated with the patient's upper and lower teeth. In use, the elastic element tends to produce extremely high forces, similar to the Herbst device, and is highly susceptible to breakage. Breakage primarily results from the ability of the device to swivel about its attachment points, producing significant flexure. This permits the device at times, to become caught between the patient's upper and lower teeth. Separation of the end caps from the connecting spring and cover is quite common as a result. Additionally, such devices produce heavy intermittent forces when the upper and lower teeth are touching and virtually no force when the mouth is resting with the upper and lower teeth slightly apart.

U.S. Pat. No. 5,435,721 (Vogt) discloses a unitary element in the form of a substantially flat plate having integral end portions. The flat elongated plate attaches to upper and lower appliances using lengths of wire and stop balls and requires a keyed wire and end portion apertures to prevent twisting. Although this device may be effective to alter teeth alignment, its multiple parts make installation cumbersome. Additionally, to accommodate a normal range of required force, at least nine different lengths of the flat plate in a variety of widths and thicknesses would be needed. This would require an extensive and expensive inventory. Further, this device uses wire having a square cross-section, and the wire must be keyed to the shape of the aperture in the end portion of the flat plate. As a result, the device would not function properly when used with upper and lower round archwires in situations where the lower arch needs to be brought forward by allowing movement about a round wire, rather than about a square wire. The archwires must be removed and reinstalled in order to place these appliances.

Consequently, the need remains to provide a device for applying appropriate continuous forces to achieve the movements that are desired for a particular treatment, and to provide devices which are less susceptible to the disadvantages of improper usage and breakage. Additionally, a need exists for a device which is easy to install without removing the archwires, and which is comfortable for the patient to wear.

Accordingly, it is an object of the present invention to substantially overcome the above-described problems.

It is another object of the present invention to provide a novel orthodontic device that attaches to existing appliances without additional ties, ligatures, or pins.

It is a further object of the present invention to provide a novel orthodontic device and method that permits adjustment after installation.

It is also an object of the present invention to provide a novel orthodontic device that can be adjusted to vary the force applied to the teeth.

It is a further object of the present invention to provide a novel orthodontic device that is rigidly fixed at an end connected to the headgear or molar tube such that no rotating, pivoting, or swiveling movement occurs at that end.

It is another object of the present invention to provide a novel orthodontic device having a folded-over end portion that mates with a non-circular or oval-shaped headgear or molar tube to preclude all relative movement therebetween, but permits axial movement of the end portion so that the end portion may be easily removed and/or inserted.

It is still an object of the present invention to provide a novel orthodontic device that lies in the plane of the patient's cheek and remains in that plane during full movement of the patient's mouth and does not protrude into the cheek or catch under the appliance or brackets or between the teeth.

It is yet another object of the present invention to provide a novel orthodontic device requiring a small number of variations in size to accommodate all patients.

It is yet a further object of the present invention to provide an orthodontic device that is comfortable to wear and permits the patient to easily clean around the device to practice proper hygiene.

It is another object of the present invention to provide an orthodontic device that applies a substantial continuous force over a wide range of mandibular movements.

SUMMARY OF THE INVENTION

The disadvantages of present orthodontic devices and methods are substantially overcome with the present invention by providing a novel orthodontic device and method for correcting overbite and underbite.

The present orthodontic device has significant features and advantages over known orthodontic devices. The device is especially easy to remove and insert, and in one embodiment requires no removal or manipulation of existing hardware. In another embodiment, simple replacement of the headgear tube or auxiliary molar tube with an oval auxiliary molar tube is required. The device is a unitary spring body that attaches to existing hardware without use of any connecting wires, pins, stop balls, ligatures and the like. Additionally, no keying is required to prevent the device from twisting and turning, as is required in some other prior art devices. In one embodiment, a folded-over end portion connects the spring body to its corresponding oval-shaped auxiliary molar tube so that no rotational, pivotal, or swiveling movement occurs at that end. When the end portion is inserted into the auxiliary molar tube, all possible movement of the end wire is prevented, while still permitting axial movement so as to facilitate quick and convenient removal and/or insertion of the end portion relative to the auxiliary molar tube. Because the device is essentially a unitary wire spring element requiring no additional connecting hardware, the device presents a minimal profile for trapping food. Accordingly, the device promotes proper hygiene and is easy to keep clean.

The novel orthodontic device attaches between the upper and lower teeth and does not pass through the imaginary line directly connecting the teeth. Thus, the device does not impinge upon the soft tissue of the mouth or upon the appliance. Since the device flexes during mandibular movement in a plane substantially parallel to the plane of the patient's cheek, the device does not protrude into the cheek. This significantly increases user comfort.

The novel orthodontic device is also cost-effective. Only three sizes or models are required to accommodate all patients from children to adults. Therefore, inventory burden is minimal. Additionally, the adjustment time is minimal as the orthodontist need only remove the device from the patient's mouth, perform the necessary "bending" adjustments, and reinsert the device between the upper and lower attachment points. This increases the orthodontist's efficiency. Additionally, some adjustments can be made to the device while worn in the patient's mouth.

The device provides a substantially continuous force throughout a wide range of mandibular movement, except at the extreme widest opening. The force applied by the device is easily adjusted by the orthodontist by bending the device to alter its effective length and applied force. A decrease in the effective length decreases the applied force and conversely, an increase in the effective length increases the applied force.

The novel orthodontic device applies a translational force between the upper and lower teeth and reduces or eliminates rotational or "tipping" forces about the tooth to which the device is attached. The longitudinal force is directed forwardly and backwardly relative to the patient's face. Thus, the teeth to which the novel device is attached may not require stabilization with an archwire attached to adjacent teeth. This permits attachment of the device where the primary teeth are being lost and replaced by permanent teeth.

More specifically, the orthodontic device for correcting overbite and underbite according to the present invention is worn in the mouth of a patient and is attached between an upper attachment means secured to the maxillary teeth and a lower attachment means secured to the mandibular teeth such that the device is proximal to the cheek of the patient.

The device is formed from a flexible resilient spring element having a generally curved body portion (when installed), and is configured to be inserted in the patient's mouth so as to lie in a plane defined by the cheek of the patient. The spring element has first and second oppositely disposed end portions where the first end portion is configured to be directly attached to corresponding upper or lower attachment means so as to preclude relative movement between the first end portion and the attachment means. The second end portion is configured to be directly attached to the other of the corresponding attachment means.

The spring element is operative to produce a pushing force between the upper and lower attachment means when attached thereto, where the body portion is configured to be shaped so as to vary the effective length of the spring element to vary the pushing force directed to the maxillary and mandibular teeth so as to displace the maxillary teeth relative to the mandibular teeth. The second end portion terminates in a loop portion configured to attach to the other of the corresponding attachment means.

BRIEF DESCRIPTION OF THE DRAWINGS

The features of the present invention which are believed to be novel are set forth with particularity in the appended claims. The invention, together with further objects and advantages thereof, may best be understood by reference to the following description in conjunction with the accompanying drawings.

DETAILED DESCRIPTION OF THE INVENTION

Figure 1:
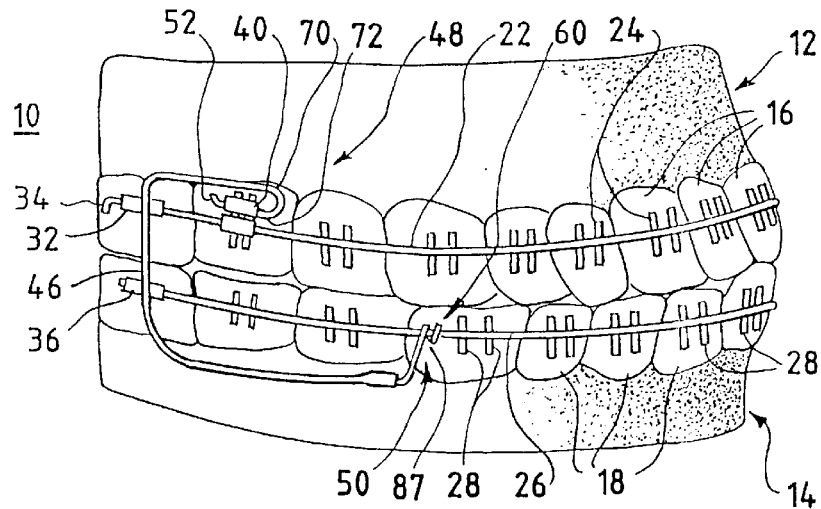
FIG. 1 is a side elevational view of a specific embodiment according to the present invention showing a spring element operatively attached to the teeth, as viewed from the side of a patient's mouth.

Referring now to FIG. 1, an orthodontic device 10 for correcting underbite and overbite is shown generally. The device 10 is shown operatively associated with an upper jaw 12 and a lower jaw 14 of a hypothetical patient. Upper teeth 16 are associated with the upper jaw 12 and lower teeth 18 are associated with the lower jaw 14. The novel orthodontic device 10 is attached between the upper or maxillary teeth 16 and the lower or mandibular teeth 18 to effect displacement of the upper teeth relative to the lower teeth.

In the illustrated embodiment, a substantially conventional upper archwire 22 is shown attached to the upper teeth 16. A plurality of vertical spaced-apart supports 24 are attached to the outer surface of each of the upper teeth 16 using bonding techniques or a suitable chemical adhesive, as is known in the art. The upper archwire 22 is appropriately interconnected between each of the vertical supports 24 using known conventional methods. A lower archwire 26 is similarly attached to the lower teeth 18 via corresponding spaced-apart vertical supports 28 attached to the lower teeth. Alternately, the vertical supports 24 and 28 may be replaced with known bands which surround each tooth.

The upper archwire 22 is received through an upper archwire molar tube 32 that is affixed to a molar of the upper teeth 16. An end 34 of the upper archwire 22 protrudes through the open end of the upper archwire molar tube 32 and is bent so as to lock the archwire in place in a conventional manner. The lower archwire 26 is secured in a similar fashion to a lower archwire molar tube 36. Such construction and attachment may employ any variety of known techniques.

The upper archwire molar tube 32 may be disposed on the first or second molar while an auxiliary molar tube 40 may be disposed on the first molar, as is dictated by the configuration of the patient's teeth 16 and 18 and the degree and type of movement desired. Alternately, the auxiliary molar tube 40 may be formed with or may be attached to the upper archwire molar tube 32, as is known in the art. Inclusion of the auxiliary molar tube 40 is conventional practice. The auxiliary molar tube 40 is typically present even if it is not used and is defined to be existing attachment hardware. The orthodontic device 10 is directly attached to the auxiliary molar tube 40, as will be described hereinafter. Note that in FIG. 1, the third molar is not shown.

Figure 2A:
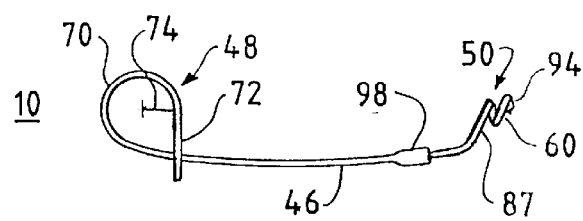
FIG. 2A is an side elevational view of a specific embodiment of a spring element.
Figure 2B:
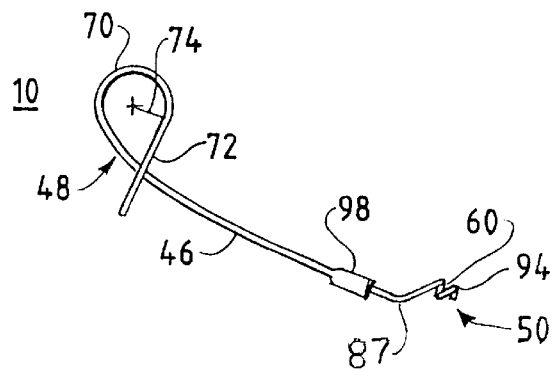
FIG. 2B is an side elevational view of the spring element of FIG. 2A tilted and viewed along the plane of a loop which terminates the second end of the spring element.

Referring now to FIGS. 1, 2A, and 2B, FIGS. 2A–2B illustrate the orthodontic device 10 in a relaxed or non-operative position when removed from the patient's mouth. The orthodontic device 10 is a flexible resilient spring element having a generally curved body portion 46 that is defined to lie in a plane relative to a plane defined by the cheek of the patient. The term "spring element 10" will be used interchangeably with the term "orthodontic device" since the device is a unitary device.

Preferably the plane of the body portion 46 is adjusted so that the device 10 is disposed in a plane substantially parallel to the plane defined by the cheek of the patient. This provides several advantages which will be described in greater detail hereinafter.

The spring element 10 has a first end portion 48 and second end portion 50 oppositely disposed from the first end portion. The first end portion 48 is configured to directly attach to the auxiliary molar tube 40 via direct insertion into the tube.

The spring element 10 may be formed from solid wire, stranded wire, or braided wire. Preferably, solid wire is used in the embodiment of FIGS. 1, 2A–2B, 4A–4B. The spring element 10 has a uniform cross-sectional diameter along its length. Preferably, such a spring element 10 is about 0.032 inches in diameter and is substantially circular. With respect to the embodiment shown in FIGS. 6A–6C, the wire is preferably formed of stranded wire having a diameter of about 0.050 inches. However, the spring element 10 may have any suitable diameter sufficient to be received within the auxiliary molar tube 40. The spring element 10 may be formed from nickel titanium alloy, nickel chrome alloy, stainless steel, or any other suitable metal. The spring element 10 is resilient but may be permanently deformed by the orthodontist by bending the wire past its elastic limit. Once in a permanently deformed configuration, subsequent flexing of the spring element 10 within its elastic range results in resilient flexing of the spring element so that a preselected amount of substantially continuous force is applied to the upper and lower teeth 16 and 18, respectively. The spring element 10 may be coated with a plastic, rubber, or other suitable coating for aesthetic reasons. According to another embodiment, the spring element is covered with a coil wire covering, as will be described in greater detail hereinafter with reference to FIG. 6A.

The spring element 10 is not limited to metal construction. Alternately, a suitable thermoplastic or fiberglass material may be used. Permanent deformation of the thermoplastic material may be performed using heating techniques after the orthodontic device 10 has been removed from the patient's mouth, as is known in the art.

Figure 3:
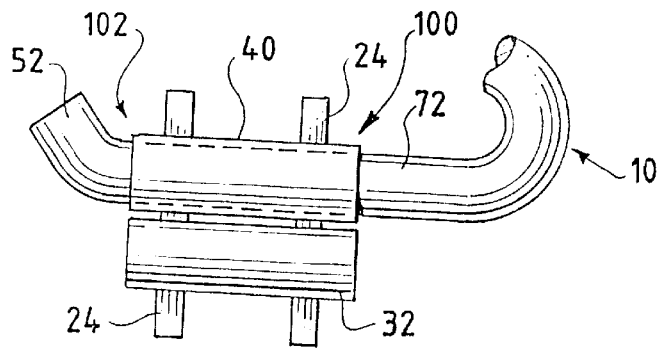
FIG. 3 is an enlarged side elevational view of the spring element of FIG. 1 particularly showing direct attachment of the spring element to an auxiliary molar tube.

Referring now to FIGS. 1 and 3, a specific embodiment is shown. FIG. 3 shows an enlarged view of the spring element 10, the upper archwire molar tube 32, and the auxiliary molar tube 40. In this illustrated embodiment, the upper archwire molar tube 32 is disposed on the same tooth as the auxiliary molar tube 40. Since the spring element 10 has a uniform cross-sectional shape, it is easily received within the auxiliary molar tube 40. An end 52 of the spring element 10 protruding through the auxiliary molar tube 40 is bent so as to lock the spring element in place. This facilitates quick and convenient removal and attachment. To remove the spring element 10, the end 52 protruding through the auxiliary molar tube 40 is simply unbent and removed from within the tube. This is a significant improvement over conventional devices which are often permanently secured around the archwires requiring time-consuming removal of the archwires.

Many prior art devices are permanently secured to the archwire by separate wires and various forms of pins and ligatures. Some devices include an aperture through which the archwire pass. To remove such a device, the archwire must be removed from the teeth. This is extremely time-consuming and cumbersome. Additionally, the patient is inconvenienced unnecessarily.

Referring now to FIGS. 1, and 2A–2B, the second end portion 50 terminates in a loop 60 configured to attach to the lower archwire 26. With the first end portion 48 directly attached to auxiliary molar tube 40 and the loop 60 of the second end portion 50 attached about the lower archwire 26, the resiliency of the spring element 10 creates a translational force that is applied to the teeth tending to backwardly displace the upper teeth 16 and forwardly displace the lower teeth 18. This corrects an overbite condition, which accounts for a majority of patient malocclusions. However, to correct an underbite condition, the attachment position of the spring element 10 is simply reversed. That is, the first end portion 48 of the spring element 10 is attached to an auxiliary molar tube disposed on a bottom molar while the second end portion 50 is attached via the loop to the upper archwire 22. Such a configuration tends to forwardly displace the upper teeth 16 and backwardly displace the lower teeth 18 to correct an underbite.

It may be seen that the orthodontic device 10 is truly a unitary device. That is, it does not require any connectors, pins, ligatures, ball stops and the like. The auxiliary molar tube 40 is typically part of the orthodontic hardware, even if it is not utilized. Thus, to implement the device 10 in a standard and typical orthodontic setting, only the spring element 10 need be added. Virtually all known "push-type" orthodontic devices use some form of additional connector such as ball stops and connecting wires to attach the device.

Additionally, no "keying" is necessary to prevent twisting and turning of the device 10, as is required in prior art devices, such as in the device described above in the Vogt patent. The orthodontic device 10 maintains its orientation within the patient's mouth and does not impinge upon the cheek or upon the soft tissue of the mouth, as will be described in greater detail hereinafter.

The first end portion 48 of the spring element 10 has a primary bend 70 which is disposed substantially within the plane of the body portion 46. In the operative position, shown in FIG. 1, the primary bend 70 preferably does not cross over itself, as is shown in FIGS. 2A and 2B. However, there may be an additional bend or helix (not shown) in the body portion 48 when space in the mouth is very limited. The primary bend 70 includes a relatively straight segment 72 which is received through the auxiliary molar tube 40. The arc or a radius of curvature 74 of the primary bend 70 is operative to vary the effective length of the spring element 10. The smaller the radius of curvature 74, the smaller the effective length of the spring element 10. Conversely, the greater the radius of curvature 74, the greater the effective length of the spring element 10. Although the actual length of the material forming the spring element 10 remains constant for a given selected size or model, regardless of how it is bent, the effective length is a measure of the way in which the spring element 10 may be resiliently deformed with respect to the amount of force produced between the attachment points (e.g., the first end portion 48 and the second end portion 50). The effective length is also a measure of how that force is applied over a wide range of jaw movement.

With the straight segment 72 received within the auxiliary molar tube 40 and the loop 60 attached about the lower archwire 26, as shown in FIG. 1, it can be seen that as the primary loop 70 is made "tighter" (i.e., the radius of curvature 74 is decreased), the amount of force applied to the teeth 16 and 18 is increased, due in part, to the spring-like resistance of the spring element 10. Conversely, it can be seen that as the primary loop 70 is "relaxed" (i.e., the radius of curvature 74 is increased), the amount of force applied to the teeth 16 and 18 is reduced. Thus, the spring element 10, and in particular, the primary loop 70 is capable of being shaped or bent in accordance with the amount of force needed to effect treatment.

The fact that a change in the effective length of the spring element 10 varies the force applied to the teeth 16 and 18 is a very significant feature of the present orthodontic device. This permits the orthodontist to rapidly and easily modify the force applied. Typically, the patient repeatedly visits the orthodontist over a period of time permitting the orthodontist to perform incremental adjustments to the orthodontic hardware to effect appropriate movement of the teeth 16 and 18. Modification of the applied force is one of the most significant adjustments performed by the orthodontist. The direction of the applied force is also very important, as will be discussed in greater detail hereinafter. To vary the effective length of the orthodontic device 10 to change the applied force, the orthodontist simply removes the spring element 10 from its attachment points and makes the appropriate modification in the primary bend 70. Given sufficient experience, the orthodontist can estimate by "feel" the amount of force applied by a particular configuration of the primary bend 70. The orthodontist increases and decreases the radius of curvature and/or the shape of the primary bend 70 to vary the effective length and, hence the force applied by the device 10. Other practitioners may use a force gauge when performing the adjustment, as is known in the art. The primary bend 70 may be adjusted between a first position, having a minimum radius of curvature, and a second position, having a maximum radius of curvature, depending upon the patient's anatomy and the force desired.

The effective length may be modified to provide an applied force to the teeth 16 and 18 in a range from about one-half ounce to ten ounces. Several basic sizes or models of the device 10 may be provided. For example, to accommodate all patients, three basic models of the device 10 may be used. Each model or size is configured to apply the required force appropriate to effect proper movement of the teeth 16 and 18. However, the number of basic models may be suitably increased or decreased to accommodate the required range of applied force in different patients and in various degrees of malocclusions. This is significant from a cost and inventory standpoint since it is relatively simple and cost-effective to have three models of the device 10 in stock at all times. Other force element devices, such as the device described above in the Vogt patent, would require at least nine different lengths, each of differing widths with each variation having differing aperture sizes. The number of permutations would be extremely high and use of such a device would require an expensive and cumbersome inventory.

The choice of models or size (length) of the orthodontic device 10 is also determined by the size of the patient's mouth, generally depending whether the patient is a child or an adult or if teeth have been extracted. Since adults have larger jaws, the jaws of an adult patient opens through a wider arc than the jaws of a child. Accordingly, a device 10 of greater length may be required when worn by an adult.

Note, that the configuration and number of strands forming the wire of the spring element 10 may also be a factor in determining the range of force applied in each of the models of the orthodontic device. For example, as the number of strands of wire used to form the spring element 10 is increased, the stiffness of the spring element is decreased, thus the applied force is decreased for that particular configuration. Even though the number of strands of wire forming the spring element 10 may vary, the outside diameter preferably remains constant within the limits of the inside diameter of the auxiliary molar tube 40, regardless of the application. Thus, all of the models of the orthodontic device 10 may have identical outside diameters and are received within the existing auxiliary molar tube 40 without requiring any modification to existing orthodontic hardware. Preferably, the spring element 10 is constructed from between six to thirty-six strands of wire wrapped around a single strand. However, the number of wrapping strands and the number of core strands may vary according to the force required and manufacturing constraints.

Figure 4A:
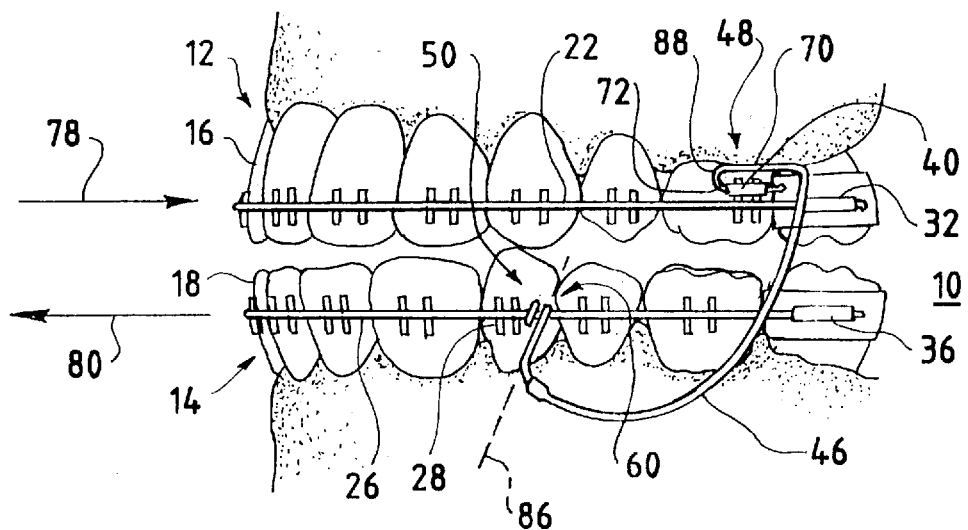
FIGS. 4A and 4B are schematic representations of a closed and open mouth, respectively, particularly illustrating placement of a loop portion of the spring element relative to the lower archwire.
Figure 4B:
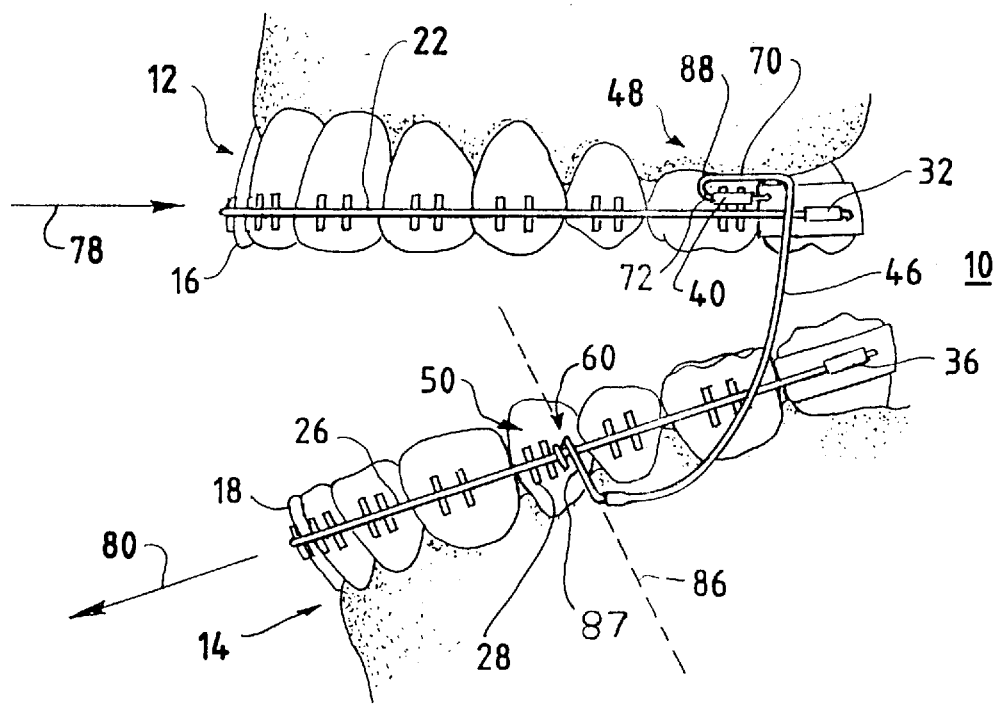

Referring now to FIGS. 1 and 4A–4B, FIGS. 4A–4B are schematic representations of the mouth of a hypothetical patient with the patient's jaws in a closed and open position, respectively. In the closed position, shown in FIG. 4A, it can be seen that the primary bend 70 permits the spring element 10 to gently curve or spiral around to where the attachment point on the second end portion 50 connects to the archwire 26. The lower archwire 26 is the lower attachment means while the auxiliary molar tube 40 is the upper attachment means. The spring element 10 is under spring stress since it is resiliently compressed when attached. Such compression results in a translational force applied to the molars tending to force the upper teeth backward and the lower teeth forward, as shown by arrows 78 and 80, respectively (FIG. 4A–4B).

Note that the loop 60 that terminates the second end portion 50 has an axis 86 that is at an angle relative to the lower archwire 26. For example, the axis 86 may be at an angle of about forty-five degrees relative to the lower archwire 26 when the jaws are in the closed position, shown in FIG. 4A. In the closed position of FIG. 4A, the loop 60 abuts against the vertical supports 28, thus providing force tending to move the lower teeth 18 forward and the upper teeth 16 backward, as shown by arrows 78 and 80. Note that the axis of the loop 60 is generally angled or canted relative to the lower archwire 26. The axis 86 or tangent of the loop 60 is permitted to move or rotate relative to the lower archwire 26 as the jaws 12 and 14 separate. Such rotation changes the angle of the axis 86 with respect to the lower archwire 26, as is shown in FIG. 4B. The axis 86, and hence the loop 60 may rotate through an angle of about ninety degrees during the full range of mandibular movement from the closed position to the fully open position of the jaws 12 and 14.

In FIG. 4B, in the open position, the spring element 10 is still under resilient stress and still applies substantially continuous translational force to the teeth 16 and 18. Again, the loop 60 abuts longitudinally against the vertical supports 28, thus providing force tending to move the lower teeth 18 forward and the upper teeth 16 backward, as indicated by arrows 78 and 80.

Note that in FIG. 4B, the position of the loop 60 and, hence the axis 86, relative to the lower archwire 26 is no longer at an approximate minus forty-five degree angle relative to the lower archwire 26. In this open configuration, the axis 86 is rotated in accordance with rotation of the loop 60 about the lower archwire 26. The loop 60 is capable of rotation about the lower archwire 26 since the loop is not fixedly attached to the lower archwire. The loop 60 freely rotates and/or swings about the lower archwire 26 while positively engaging the lower archwire within the loop. Such rotation of the loop 60 about the lower archwire 26 permits the spring element 10 to apply substantially continuous force to the teeth 16 and 18 whether the jaws of the patient are in the open position or the closed position.

As the loop 60 rotates or swings about the lower archwire 26 during the full range of mandibular movement, the loop may also slide forward and backward along the lower archwire between the two "stops" or vertical supports 28 between which the loop is positioned. Additionally, the force applied by the spring element 10 is substantially continuous throughout almost all of the full range of mandibular movement.

Further, in the closed position shown in FIG. 4A, the axis 86 is canted backwardly at about a minus forty-five degree angle. Thus, when the jaws are moved from the most closed position to the most open position, the axis 86 rotates from minus forty-five degrees to about plus forty-five degrees. Thus, an approximately ninety degree rotation of the loop 60 occurs. Note that in the FIGS. 4A–4B, the angles are not drawn to scale. The loop 60 also includes a loop bend 87 (FIG. 2A) which is substantially within the plane of the body portion 46. The loop bend 87 in conjunction with the primary bend 70 is operative to vary the effective length of the spring element 10. Thus, the orthodontist adjusts and configures the primary bend 70 and the loop bend 80 to vary the effective length, and hence the applied force.

Another important feature of the loop 60 is that it permits the plane of the body portion 46 to remain essentially parallel to the plane of the patient's cheek. This is extremely important for reasons of user comfort. Known orthodontic devices, such as those described above, tend to budge outward into the patient's cheek as the patient chews. Thus, each time the patient closes his or her mouth, the device protrudes into the cheek. This may cause discomfort and annoyance. Additionally, such movement of known devices may allow the patient to inadvertently bite the device causing possible damage to the device and to the patient's teeth. Due, in part, to rotation of the loop 60, all flexing and resilient deformation of the spring element 10 in the present novel device occurs in a plane parallel to the cheek of the patient. Accordingly, the orthodontic device 10 remains substantially parallel to the cheek and parallel to the upright surfaces or side edges of the teeth 16 and 18 as the patient chews, and does not protrude or bulge into the cheek.

Figure 5:
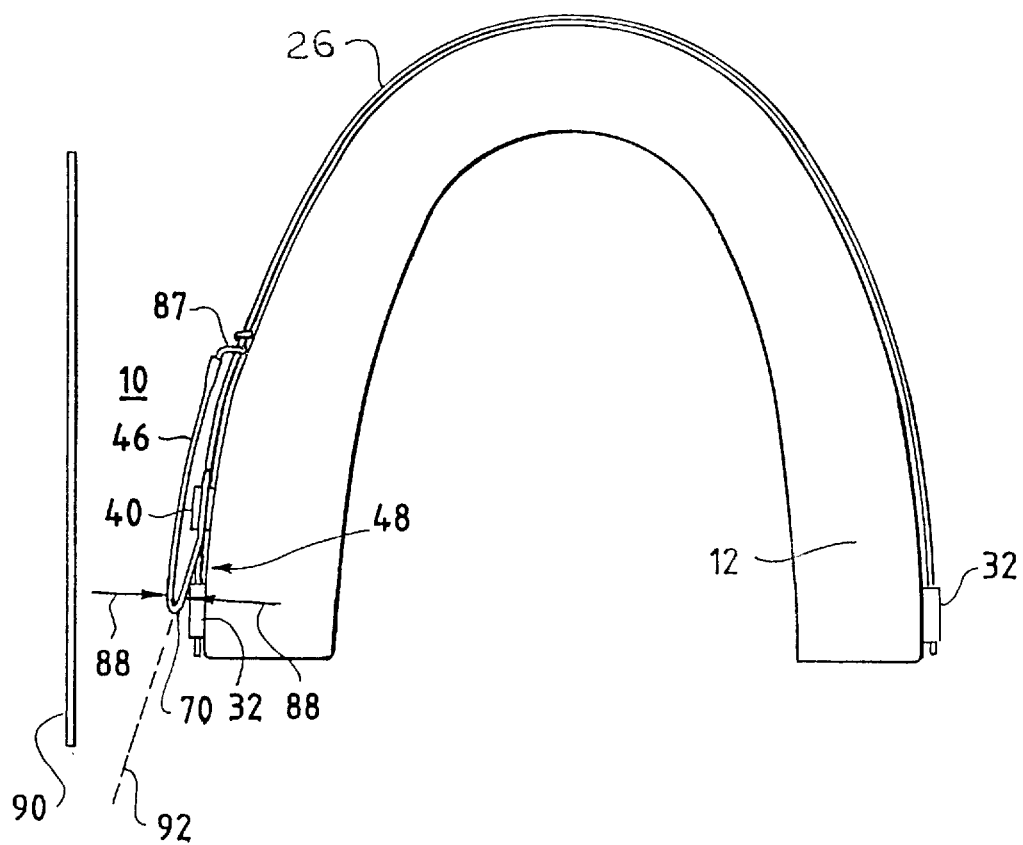
FIG. 5 is a top view of an upper jaw or arch particularly illustrating the profile of the spring element relative to the plane of the cheek of the patient.

Referring now to FIG. 5, a top view of the upper jaw or arch 12 is shown particularly illustrating the profile of the spring element 10 relative to the plane of the cheek, indicated as reference numeral 90. Another reason why the plane of the body portion 46 remains substantially parallel to the plane 90 of the cheek is that the spring element 10 includes an additional critical bend or secondary bend 88. The secondary bend 88 is disposed proximal to the primary bend 70. The secondary bend 88 is substantially perpendicular to the plane of the primary bend 70 and may be oriented laterally, either toward or away from the cheek of the patient, as is indicated by the arrows 88. The secondary bend 88 is effective to orient or position the plane of the body portion 46 so that it is operatively disposed in a plane substantially parallel to the plane defined by the cheek 90 of the patient. The secondary bend 88 is configured to vary the plane of the body portion 46 relative to the plane of the cheek 90 of the patient, as shown by line 92 (when the mouth is fully open).

Referring now to FIGS. 1 and 2A–2B, it is noted that the loop 60 may be formed as an open loop, a spiral loop, or a substantially closed loop. As shown in the illustrated embodiment, the loop 60 is preferably a spiral loop such that the extreme end of the loop does not contact itself. Thus, the loop 60 has a partially open portion 94 (FIGS. 2A and 2B) such that the open portion is "skewed" away from itself and does not reside in the plane of the loop. This permits the orthodontist to easily and quickly attach and detach the loop 60. The orthodontist manipulates the angle of the loop 60 so that the open portion 94 of the loop 60 engages the lower archwire 26. This essentially "captures" the archwire within the loop 60. Once in position, the loop 60 cannot become disengaged from the lower archwire 26 since the force exerted by the spring element 10 between the loop 60 and the vertical supports 28 (FIG. 1) against which it abuts. Only intentional and specific manipulation of the orthodontic device 10 permits removal of the loop 60 from the lower archwire 26. As discussed above, as the patient chews, the loop 60 rotates or swings about the lower archwire 26. During such rotation or swinging, the open portion 94 of the loop 60 is prevented from being disengaged therefrom. The partially open spiral loop 60 configuration is preferred since a fully closed loop would require the additional step of opening the loop with a suitable tool for removal and crimping or closing the loop after installation. Note that loop 60 may be separate but fixedly attached to the spring element 10. As shown in FIGS. 2A–2B, a crimped cap portion 98 or connecting tube may connect the loop 60 to the spring element 10. However, any suitable form of connector may connect the loop 60 to the spring element 10.

Referring now to FIGS. 1 and 3, note that the straight segment 72 received within the auxiliary molar tube 40 is received within a forward end 100 (FIG. 3) of the auxiliary molar tube rather than within a rearward end 102 (FIG. 3). This is a significant feature for at least two reasons. First, attachment to the forward end 100 of the auxiliary molar tube 40 facilitates easy an rapid attachment since attachments further back in the mouth of the patient are more difficult to perform due to space constraints. Second, attachment at the forward end 100 of the auxiliary molar tube 40 permits the primary bend 70 to spiral backward avoiding intersecting an imaginary line connecting the upper and lower attachment points (i.e., the auxiliary molar tube 40 and the loop 60). This configuration allows for easy adjustment of the effective length of the spring element 10 where such adjustment does not create a situation where the spring element impinges upon the teeth, the existing orthodontic appliances, or the soft tissue of the patient's mouth. This configuration, having a backward spiral, permits use of a relatively long length of spring element material 10 relative to the amount of space available in the patient's mouth so the patient is permitted a full range of mandibular movement. This significantly increases the range through which the orthodontic device 10 applies substantially continuous force to the teeth 16 and 18.

Because the first end 48 of the spring element 10 is received directly within the auxiliary molar tube 40, the mechanics of the spring element differ from that of known spring-type orthodontic devices. Prior art devices are typically pinned to the auxiliary molar tube from the outer aspect or the rearward end 102 (FIG. 3) of the auxiliary molar tube. Alternately, these prior art devices may be anchored to an archwire which connects the molar to the adjacent tooth. Such a configuration creates a "tipping" force or rotational moment about the center of resistance of the tooth. The center of resistance of the molar tooth is below the level of the gum and toward the root of the tooth. Such tipping force is usually undesirable if only translational force need be applied. Prior art devices counteract the effect of the tipping force by stabilizing that tooth with the archwire connected to adjacent teeth. Thus, known prior art devices must always stabilize the anchor tooth by rigid connection to the archwire.

Since the spring element 10 of the present device is attached directly into the auxiliary molar tube 40 and applies a spring force to the tooth, a "lever arm" is formed. The opposite end 50 (second end—FIG. 1) is attached to the lower archwire 26 via the loop 60, and raising or lowering the lever arm creates a "couple" which produces a force moment balancing the tipping force. The spring element may be configured so that it only produces translational forces (arrows 78 and 80 of FIG. 4A–4B) on the teeth 16 and 18 without producing tipping or rotational forces. If a tipping force is desired, the spring element 10 may also be configured to provide it by varying the ratio of compressive force to lifting force effected by changing the length and shape of the spring element 10, as described. This is significant since the orthodontic device 10 may be affixed to a tooth that may not be stabilized by connection to an archwire. This is useful where the primary teeth are being lost and replaced with permanent teeth.

Figure 6A:
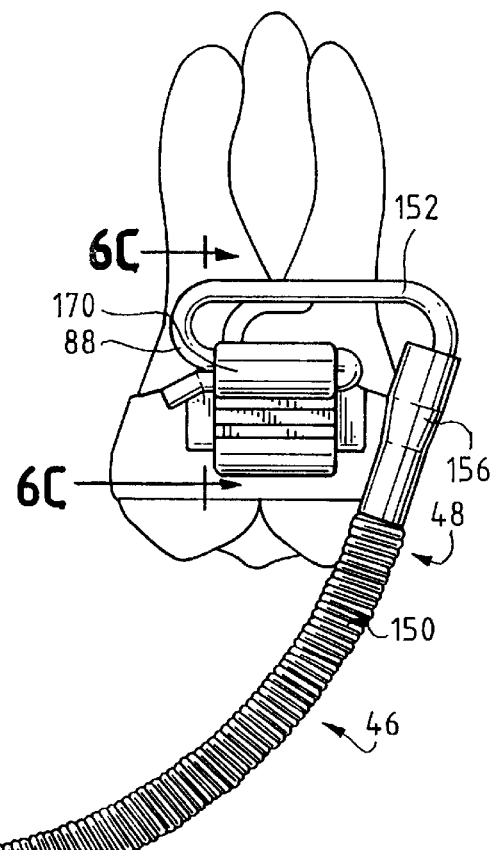
FIG. 6A is a side elevational view of a preferred embodiment of a spring element having a folded end portion for rigidly attaching the spring element to its attachment means.

Referring now to FIGS. 1, and 6A–6C, FIGS. 6A–6C show a preferred embodiment of the spring element 10, including the first end portion, shown generally as 48, and the second end portion, shown generally as 50, particularly showing the way in which the first end portion is attached to its attachment point via end wires, as will be described below. As shown in FIG. 6A, the curved body portion 46 includes an outer coiled wire sheath 150, which promotes user comfort by increasing the effective diameter of the body portion. The stranded wire spring element 10 within the sheath 150 is not visible in FIG. 6A, but is the same as described above with respect to FIG. 1, except for its extreme ends, as will be described hereinafter. The sheath 150 also functions to capture any strands of wire that may inadvertently break so that the broken strands do not impinge on the soft tissue of the mouth. The body portion 46 is the same as described above with respect to the primary bend, therefore such discussion is not repeated here.

The first end portion 48 is connected to a first end wire 152, and the second end portion 50 is connected to a second end wire 154, via corresponding connecting tubes 156 disposed at each end of the spring wire 10. The connecting tubes 156 are crimped or soldered to form a unitary connection between the spring element 10 and the corresponding end wires 152 and 154. Thus, the body portion 46 appears as a unitary structure even though it is formed from more than one section of metal or other suitable material.

Note that the majority of the pushing force effective to move the teeth is imparted by the spring element 10, while only a very small portion of such pushing force is contributed by the coiled wire sheath 150. Also note that the coiled wire sheath 150 is not fixedly attached to the inner spring element 10, and is not fastened to opposite connecting tubes 156. Rather, the coiled wire sheath 150 "rides" over the spring element 10 and slides between the two connecting tubes 156. The coiled wire sheath 150 is an open coil compression spring. That is, adjacent coils do not touch. Rather, the end coils of the sheath 150 gently press against the corresponding connecting tube 156, and the sheath 150 compresses as the spring element 10 is flexed.

Figure 6B:
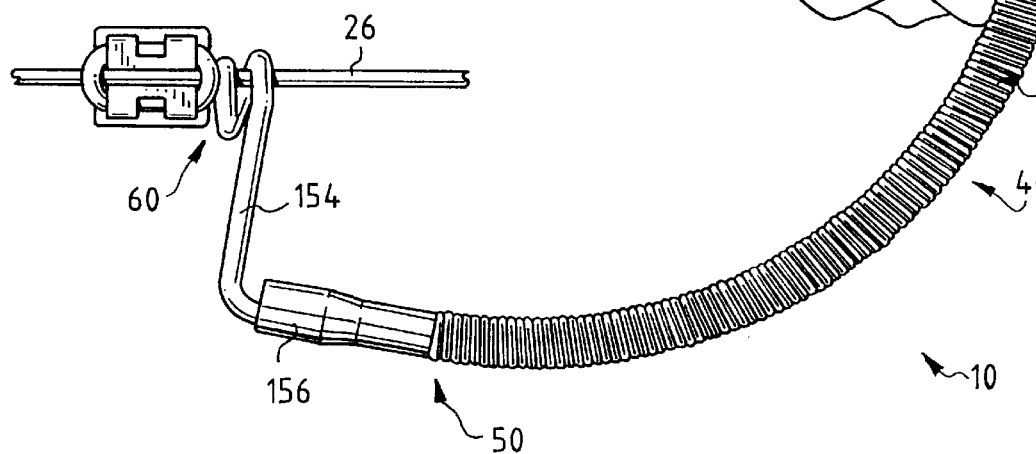
FIG. 6B is an enlarged unobstructed view of a folded end portion of the spring element shown in FIG. 6A.
Figure 6B:
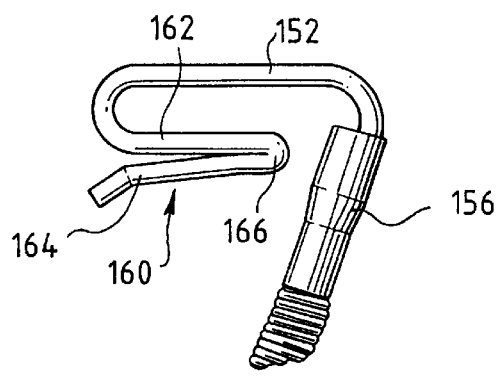

As more clearly shown in FIG. 6B, the first end wire 154 is bent so as to have a "folded-over" portion 160. The folded portion 160 is formed of two lengths of wire 162 and 164 connected by a single bend 166, where each length of wire substantially contacts the other length of wire tangentially along an axis of the lengths of the wires. As shown more clearly in the cross-sectional view of FIG. 6C, the folded end wire 160 has an effective rectangular cross-sectional shape, and appears as two tangential circles in FIG. 6C. Essentially, its outline resembles a rectangle. However, tangential contact may not always exist if the two lengths of wire 162 and 164 outwardly diverge from the common bend 166. In this situation, the spring tension created by the two lengths of wires 162 and 164 also contributes to facilitate a rigid and immobile connection within an auxiliary molar tube 170. Alternately, the cross-sectional shape of the end wire 152 may be inherently square or rectangular, meaning that the end wire itself may be formed of wire with such a cross-sectional shape.

Figure 6C:
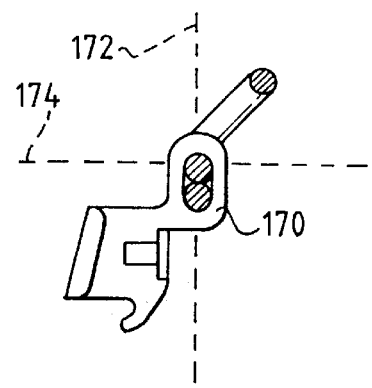
FIG. 6C is an enlarged cross-sectional view of an attachment means for receiving the folded end portion shown in FIG. 6A.

The auxiliary molar tube 170 shown in FIG. 6C is similar to the auxiliary molar tube 40 of FIG. 1, except that its cross-sectional shape is non-circular. Specifically, the cross-sectional shape of the auxiliary molar tube 170 is oblong or oval. This creates an effective rectangular shape so that when the folded end wire 160 is inserted into the auxiliary molar tube 170, a frictional fit is formed therebetween, which essentially "locks" the end wire 152 within the auxiliary molar tube to form a rigid and immobile connection. Preferably, the height of the auxiliary molar tube 170 along its long axis 172 is about twice the diameter of the first end wire 152, while the width of the auxiliary molar tube along its short axis 174 is about equal to the diameter of the first end wire. Thus, when the folded end wire 160 is inserted into the auxiliary molar tube 170, the folded end wire occupies substantially the entire inside area or volume of the auxiliary molar tube forming a frictional fit. Because of the frictional fit and the relative dimensions of the folded end wire 160 and auxiliary molar tube 170, the folded end wire cannot pivot, swivel, or rotate relative to the auxiliary molar tube. All possible relative movement is precluded, except of course that transverse or axial movement is permitted, which permits the folded end wire 160 to be easily and quickly inserted into and removed from the auxiliary molar tube 170. Should the folded end wire 160 inadvertently become loose within the auxiliary molar tube 170 due to slight deformation of the auxiliary molar tube over time and with prolonged use, the folded end wire may be removed and the wire lengths 162 and 164 expanded so as to increase the angle between the two lengths of wire so that they diverge slightly from the bend 166. Additionally, the auxiliary molar tube 170 may be reshaped or "tightened." Upon reinsertion of the folded end wire 160 into the auxiliary molar tube 170, a tight, rigid, and immobile connection will again be established because of the spring tension exerted by the folded end wire against the inside surface of the auxiliary molar tube.

As shown in FIG. 6A, the second end wire 154 includes a helical loop 60, which may be the same as the loop described previously with respect to FIGS. 1, 2A–2B, and 4A–4B. Alternatively, the second end wire 154 may include means to permit the body portion 46 to rotate or swivel relative to its attachment point on the corresponding arch wire 26 (FIG. 1). Such means may include a fixed end cap fixedly attached to one end of the body portion 46 having an aperture for receiving a wire stub. The wire stub is connected to the arch wire at one end, and to a small metal ball at the other end. This arrangement permits the end cap (and therefore, the body portion at that end only) to swivel about the wire stub and bear against the round ball. Other mechanisms may also be used to permit the second end wire to swivel or pivot relative to its lower attachment means. Proper orientation of the device 10 is maintained as long as one attachment point remains rigid and immobile (the folded end wire 160 and auxiliary molar tube 170), while the opposite end of the device is free to pivot, rotate, or swivel relative to its attachment means. The above preferred description of the folded end wire 162 and auxiliary molar tube 170, as shown in FIGS. 6A–6C, is implemented in the environment shown in FIGS. 1, 4A–4B, and 5.

Referring now to FIGS. 1 and 6A, in operation, the orthodontist determines the desired effective length of the spring element 10 and adjusts the shape or radius of the primary bend 70 (FIGS. 1, 2A, 2B, 4A, and 4B) and the loop bend 88 to correspond to the desired effective length. The effective length may also be changed by changing the shape or angle of one or both end wires 152 and 154, for example, at a point proximal to the corresponding connecting tubes 156. Note that such variation also changes the applied force. The effective length is operative to vary the applied forced directed toward the upper and lower teeth 16 and 18. Once the primary bend 70 and the loop bend 87 have been configured, the orthodontist places the spiral loop 60 proximal the lower archwire 26 so that the loop engages the lower archwire and cannot be inadvertently removed therefrom. The spiral loop 60 is inserted from outside of the mouth so that the open portion of the loop engages the lower archwire 26. The spring element 10 is then upwardly rotated so that the spiral loop 60 captures the lower archwire 26, thus rotatably locking the loop 60 about the lower archwire. The body portion 46 of the spring element 10 is then rotated into the plane of the patient's cheek essentially permitting the entire spring element 10 to be positioned within the mouth of the patient.

Next, with respect to FIG. 1, the orthodontist directly connects the straight portion 72 of the spring element 10 to the auxiliary molar tube 40 and bends the end of the straight segment protruding through the tube, so as to lock the spring element in place. With respect to the preferred embodiment shown in FIG. 6A, the orthodontist directly inserts the folded wire portion 160 into the auxiliary molar tube 170. The end wire 152 is locked in place within the auxiliary molar tube 170 due to its frictional fit. After the spring element 10 is secured to its attachment points, the plane of the body portion 46 may then be adjusted so that it is parallel to the plane of the patient's cheek by appropriate modifications of the secondary bend 88. Other adjustments may also be made to the device 10 while it is worn in the patient's mouth.

Specific embodiments of an orthodontic device and method according to the present invention have been described for the purpose of illustrating the manner in which the invention may be made and used. It should be understood that implementation of other variations and modifications of the invention and its various aspects will be apparent to those skilled in the art, and that the invention is not limited by the specific embodiments described. It is therefore contemplated to cover by the present invention any and all modifications, variations, or equivalents that fall within the true spirit and scope of the basic underlying principles disclosed and claimed herein.

What is claimed is:

1. An orthodontic device for wearing in a mouth of a patient, the device adapted for attachment between an upper attachment means secured to an upper, tooth and a lower attachment means secured to a lower tooth, the device proximal a cheek of a patient, the device comprising:

a flexible resilient spring element having a body portion arranged to lie in a plane defined by the cheek of the patient;

the spring element having first and second oppositely disposed end portions;

said first end portion configured to be directly attached to at least one of the upper and lower attachment means so as to preclude relative movement between the first end portion and the corresponding attachment means;

said second end portion having a loop portion configured to attach to the other of the corresponding attachment means to permit relative movement between the second end portion and said other of the corresponding attachment means; and said spring element operative to produce a pushing force between the upper and lower attachment means operative to displace the upper teeth relative to the lower teeth, and configured to be shaped so as to vary an effective length of the spring element to vary the pushing force directed to the upper and lower teeth.

2. The device according to claim 1 wherein the first end portion has a non-circular cross-sectionally shaped termination portion configured to be retained within the corresponding attachment means so as to rigidly fix the first end portion relative to said corresponding attachment means and prevent relative movement therebetween.

3. The device according to claim 2 wherein at least one of the upper and lower attachment means has a non-circular cross-sectional shape so as to rigidly receive the termination portion and prevent relative movement therebetween.

4. The device according to claim 3 wherein at least one of the upper and lower attachment means has a substantially oval cross-sectional shape.

5. The device according to claim 1 wherein the first end portion includes a folded end portion having an effective rectangular cross-sectional shape.

6. The device according to claim 5 wherein at least one of the upper and lower attachment means has an effective rectangular cross-sectional shape corresponding to the effective cross-sectional shape of the folded end portion such that insertion of the folded end portion into the corresponding attachment means prevents relative movement therebetween.

7. The device according to claim 5 wherein the folded end portion forms a frictional fit with said corresponding attachment means so as to prevent rotating, pivoting, and swiveling of the folded end portion relative to said corresponding attachment means.

8. The device according to claim 5 wherein the folded end portion is formed of two lengths of wire connected by a single bend, each length of wire substantially contacting the other length of wire tangentially along an axis of the lengths of wire.

9. The device according to claim 5 wherein the folded end portion is formed of a length of wire having a non-circular cross-sectional shape.

10. The device according to claim 5 wherein the folded end portion is formed of two lengths of wire connected to each other at a predetermined angle forming a V-shaped portion configured to be received within at least one of the upper and lower attachment means.

11. An orthodontic device for wearing in a mouth of a patient, the device adapted for attachment between an upper attachment means secured to an upper tooth, and a lower attachment means secured to a lower tooth, the device proximal a cheek of a patient, the device comprising:

a flexible resilient spring element having a body portion arranged to lie in a plane defined by the cheek of the patient;

the spring element having first and second oppositely disposed end portions;

said first end portion configured to be directly attached to at least one of the upper and lower attachment means so as to preclude relative movement between the first end portion and the corresponding attachment means;

said second end portion configured to be directly attached to the other of the corresponding attachment means so as to permit the second end portion to rotate or swivel relative to said other corresponding attachment means; and the spring element operative to produce a pushing force between the upper and lower attachment means operative to displace the upper teeth relative to the lower teeth, and configured to be shaped so as to vary an effective length of the spring element to vary the pushing force directed to the upper and lower teeth.

12. The device according to claim 11 wherein the first end portion has a non-circular cross-sectionally shaped termination portion configured to be retained within the corresponding attachment means so as to rigidly fix the first end portion relative to said corresponding attachment means and prevent relative movement therebetween.

13. The device according to claim 12 wherein at least one of the upper and lower attachment means has a non-circular cross-sectional shape so as to rigidly receive the termination portion and prevent relative movement therebetween.

14. The device according to claim 11 wherein the first end portion includes a folded end portion having an effective rectangular cross-sectional shape.

15. The device according to claim 14 wherein at least one of the upper and lower attachment means has an effective rectangular cross-sectional shape corresponding to the effective cross-sectional shape of the folded end portion such that insertion of the folded end portion into the corresponding attachment means prevents relative movement therebetween.

16. The device according to claim 15 wherein at least one of the upper and lower attachment means has a substantially oval cross-sectional shape.

17. The device according to claim 14 wherein the folded end portion forms a frictional fit with said corresponding attachment means so as to prevent rotating, pivoting, and swiveling of the folded end portion relative to said corresponding attachment means.

18. The device according to claim 14 wherein the folded end portion is formed of two lengths of wire connected by a single bend, each length of wire substantially contacting the other length of wire tangentially along an axis of the lengths of wire.

19. The device according to claim 14 wherein the folded end portion is formed of a length of wire having a non-circular cross-sectional shape.

20. The device according to claim 14 wherein the folded end portion is formed of two lengths of wire connected to each other at a predetermined angle forming a V-shaped portion configured to be received within at least one of the upper and lower attachment means.

* * * * *

UNITED STATES PATENT AND TRADEMARK OFFICE
CERTIFICATE OF CORRECTION

PATENT NO. : 5,846,074
DATED : December 8, 1998
INVENTOR(S) : Klapper et al.

It is certified that error appears in the above-indentified patent and that said Letters Patent is hereby corrected as shown below:

On the title page, under item [19], insert --et al--, after "Klapper"; and item [76] should read--  Lewis Klapper, 744 Falls Circle, Lake Forest, Illinois 60045 ;  Richard George, 930 Burridge Court, Libertyville, Illinois 60048.

Signed and Sealed this

Thirteenth Day of July, 1999

Attest:

Q. TODD DICKINSON

Attesting Officer

Acting Commissioner of Patents and Trademarks